United States Patent
Fujio et al.

[11] Patent Number: 5,873,828
[45] Date of Patent: Feb. 23, 1999

[54] ULTRASONIC DIAGNOSIS AND TREATMENT SYSTEM

[75] Inventors: Kouji Fujio, Hachioji; Isami Hirao, Hino; Sakae Takehana, Machida; Yasuhiro Ueda, Kokubunji; Takashi Tsukaya, Hachioji; Yoshinao Oaki, Hino, all of Japan; Seiji Kuramoto, Woodbury, N.Y.

[73] Assignee: Olympus Optical Co., Ltd., Tokyo, Japan

[21] Appl. No.: 387,490

[22] Filed: Feb. 13, 1995

[30] Foreign Application Priority Data

Feb. 18, 1994 [JP] Japan ..................................... 6-021224

[51] Int. Cl.[6] ........................................................ A61B 8/12
[52] U.S. Cl. ......................... 600/439; 600/459; 600/461; 600/471
[58] Field of Search ............................ 128/660.03, 653.1, 128/660.01, 662.05, 662.06, 662.03; 601/2; 600/103, 104, 109, 114, 160, 407, 439, 437, 466, 471, 472, 464, 459

[56] References Cited

U.S. PATENT DOCUMENTS

| | | |
|---|---|---|
| 4,742,829 | 5/1988 | Law et al. ............................ 128/662.05 |
| 4,763,662 | 8/1988 | Tokoi .................................. 128/662.05 |
| 4,874,376 | 10/1989 | Hawkins et al. ......................... 128/772 |
| 5,117,832 | 6/1992 | Sanghvi et al. . |
| 5,188,111 | 2/1993 | Yates et al. .............................. 128/657 |
| 5,209,721 | 5/1993 | Wilk ................................... 128/662.05 |
| 5,261,889 | 11/1993 | Laine et al. .............................. 600/104 |
| 5,273,027 | 12/1993 | Sekino et al. . |
| 5,345,940 | 9/1994 | Seward et al. ...................... 128/662.06 |
| 5,398,685 | 3/1995 | Wilk et al. ............................ 128/653.1 |
| 5,398,690 | 3/1995 | Batten et al. ....................... 128/662.05 |
| 5,421,336 | 6/1995 | De Bernardis ...................... 128/662.05 |
| 5,499,630 | 3/1996 | Hiki et al. ............................... 600/104 |

FOREIGN PATENT DOCUMENTS

| | | |
|---|---|---|
| 3919592 | 2/1990 | Germany . |
| 3934644 | 4/1990 | Germany . |
| 3618906 | 12/1993 | Germany . |
| 9318282 | 1/1994 | Germany . |
| 62-127050 | 6/1987 | Japan . |
| 5-74373 | 10/1993 | Japan . |
| 93/08738 | 5/1993 | WIPO . |
| 93/16641 | 9/1993 | WIPO . |

*Primary Examiner*—Brian Casler
*Attorney, Agent, or Firm*—Armstrong, Westerman, Hattori, McLeland & Naughton

[57] ABSTRACT

An ultrasonic diagnosis and treatment system having a thin tube which is capable of being inserted into a body cavity, and which has at its extreme end an observing ultrasonic vibrator for emitting ultrasonic waves for observation and a treating ultrasonic vibrator for emitting strong ultrasonic waves for treatment. Observation and treatment are performed by using ultrasonic wave. The system further includes a processing device for performing an operation other than the ultrasonic treatment at least on a region observed by using ultrasonic waves. A guide for enabling the processing device to reach the region observed by using ultrasonic waves is provided on the thin tube.

34 Claims, 7 Drawing Sheets

ULTRASONIC DIAGNOSIS AND TREATMENT SYSTEM

BACKGROUND OF THE INVENTION

1. Field of the Invention

The present invention relates to an ultrasonic diagnosis and treatment system having an ultrasonic probe for making ultrasonic diagnosis and ultrasonic treatment with converged ultrasonic waves in a body cavity.

2. Description of the Related Art Statement

Various ultrasonic diagnosis apparatuses have been proposed which are generally arranged to display, as a visible ultrasonic tomographic image, information collected in a plurality of directions in a living body by repeatedly transmitting ultrasonic pulses from an ultrasonic vibrator to organic tissues of the living body, by receiving ultrasonic pulse echoes reflected by the organic tissue with the same ultrasonic vibrator or a different ultrasonic vibrator separately provided and by gradually shifting the directions in which the ultrasonic pulses are transmitted and received.

In general, such ultrasonic diagnosis apparatuses are of the type using extracorporeal ultrasonic probes. However, intracorporeal ultrasonic probes, such as an ultrasonic probe combined with an endoscope, a small-diameter ultrasonic probe and an in-coelom ultrasonic probe capable of being inserted into body cavities, have also been used widely.

On the other hand, various ultrasonic treatment apparatuses for making various treatments with converged ultrasonic waves, e.g., calculus crushing apparatuses and ultrasonic thermatologic apparatuses, have also been proposed. Among such treatment apparatuses using ultrasonic waves, ultrasonic high-temperature treatment apparatuses are known which treat a lesion in organic tissues such as cancerous cells by instantaneously cauterizing the same at a high temperature by strongly converged ultrasonic waves.

Ultrasonic high-temperature treatment apparatuses of this kind include one which converges ultrasonic waves to a target part from an extracorporeal applicator having a large-opening ultrasonic vibrator to obtain strong converged ultrasonic waves, and one incorporating a comparatively small ultrasonic vibrator and having an in-coelom ultrasonic probe inserted in the rectum to treat the prostate hypertrophied.

An ultrasonic treatment apparatus disclosed in the publication of PCT WO93/16641 is combined with a positioning means for positioning a deep treated part (a focal point to which treating ultrasonic waves are converged), e.g., an ultrasonic diagnosis apparatus for obtaining an ultrasonic tomographic image. If, as in such a case, a diagnosing ultrasonic vibrator for focal point positioning is incorporated in the above-described extracorporeal applicator or in-coelom ultrasonic probe for ultrasonic treatment, positioning of a treated part can easily be performed with an ultrasonic tomographic image, and a treatment with ultrasonic waves can be reliably made while making ultrasonic diagnosis.

The application of the above-described conventional ultrasonic high-temperature treatment apparatus, particularly those having an in-coelom probe inserted in the rectum to treat the prostate is disadvantageously restricted and cannot be used by inserting the probe in lumina other than the rectum, because the probe is large in diameter and hard and because the end of the probe from which diagnosing and treating ultrasonic waves are radiated cannot be freely curved.

Thus, the conventional apparatuses for performing ultrasonic diagnosis and ultrasonic treatment can be applied only to restricted parts depending upon the construction of the ultrasonic probe having the ultrasonic vibrator for radiating diagnosing and treating ultrasonic waves, and they cannot be used to make in-coelom high-temperature treatment by inserting the probe into an upper or lower digestive tube, the thoracic cavity, the abdominal cavity, a cerebral ventricle or the like. The conventional apparatuses are also unsatisfactory in terms of treatment efficiency, because they only utilize ultrasonic wave energy by emitting treating ultrasonic waves.

Further, since the conventional apparatuses are arranged for inserting only a single ultrasonic probe unit into body cavities, they are not capable of detecting and monitoring various kinds of information on the position at which treating ultrasonic waves are converged or internal body portions in the vicinity of a treated part (the body temperature of the treated part, the intensity of ultrasonic waves at the treated part, etc.), so that it is difficult for an operator to make a treatment safely and reliably by grasping treatment situations.

SUMMARY OF THE INVENTION

An object of the present invention is to provide an ultrasonic diagnosis and treatment system capable of inserting a thin diagnosing and treating tube into a desired part in a body cavity to conduct a treatment and other kinds of operation with ultrasonic waves to treat the diseased part efficiently and reliably.

Another object of the present invention is to provide an ultrasonic diagnosis and treatment system capable of simultaneously making a treatment with ultrasonic waves and a treatment by other means to improve the effect of treating the diseased part in comparison with the case of making a treatment only by ultrasonic waves.

Still another object of the present invention is to provide an ultrasonic diagnosis and treatment system capable of performing operation for assisting an ultrasonic treatment to improve the effect of treating the diseased part as well as to improve the reliability of the treatment.

A further object of the present invention is to provide an ultrasonic diagnosis and treatment system capable of detecting and monitoring various information on a treated parts and other internal body portions at the time of treatment with ultrasonic waves to make a treatment reliably while easily grasping treatment situations, whereby the treatment reliability and the safety for living bodies can be improved.

To achieve these objects, according to the present invention, there is provided an ultrasonic diagnosis and treatment system for performing observing and treating operations using ultrasonic waves, the system having a thin tube capable of being inserted into a body cavity, the thin tube having at its extreme end an observing ultrasonic vibrator for emitting ultrasonic waves for observation and a treating ultrasonic vibrator for emitting strong ultrasonic waves for treatment. The system comprises operation means for performing an operation other than the treating operation using the ultrasonic waves at least on a region observed by using the ultrasonic waves, and an operation means guide provided on the thin tube to enable the operation means to reach the region observed by using the ultrasonic waves.

The above and other objects, features and advantages of the present invention will become apparent from following detailed description of preferred embodiments thereof taken in conjunction with the accompanying drawings.

BRIEF DESCRIPTION OF THE DRAWINGS

FIGS. 1 through 7 illustrate a first embodiment of the present invention;

FIGS. 9 through 13 illustrate a second embodiment of the present invention;

DESCRIPTION OF THE PREFERRED EMBODIMENTS

The first embodiment of the present invention will be described below with reference to FIGS. 1 through 7.

In this embodiment, the construction of an ultrasonic probe having diagnosing and treating ultrasonic vibrators is applied as a thin tube inserted for diagnosis and treatment in body cavities to an endoscope having an optical observation function.

Figure 1:
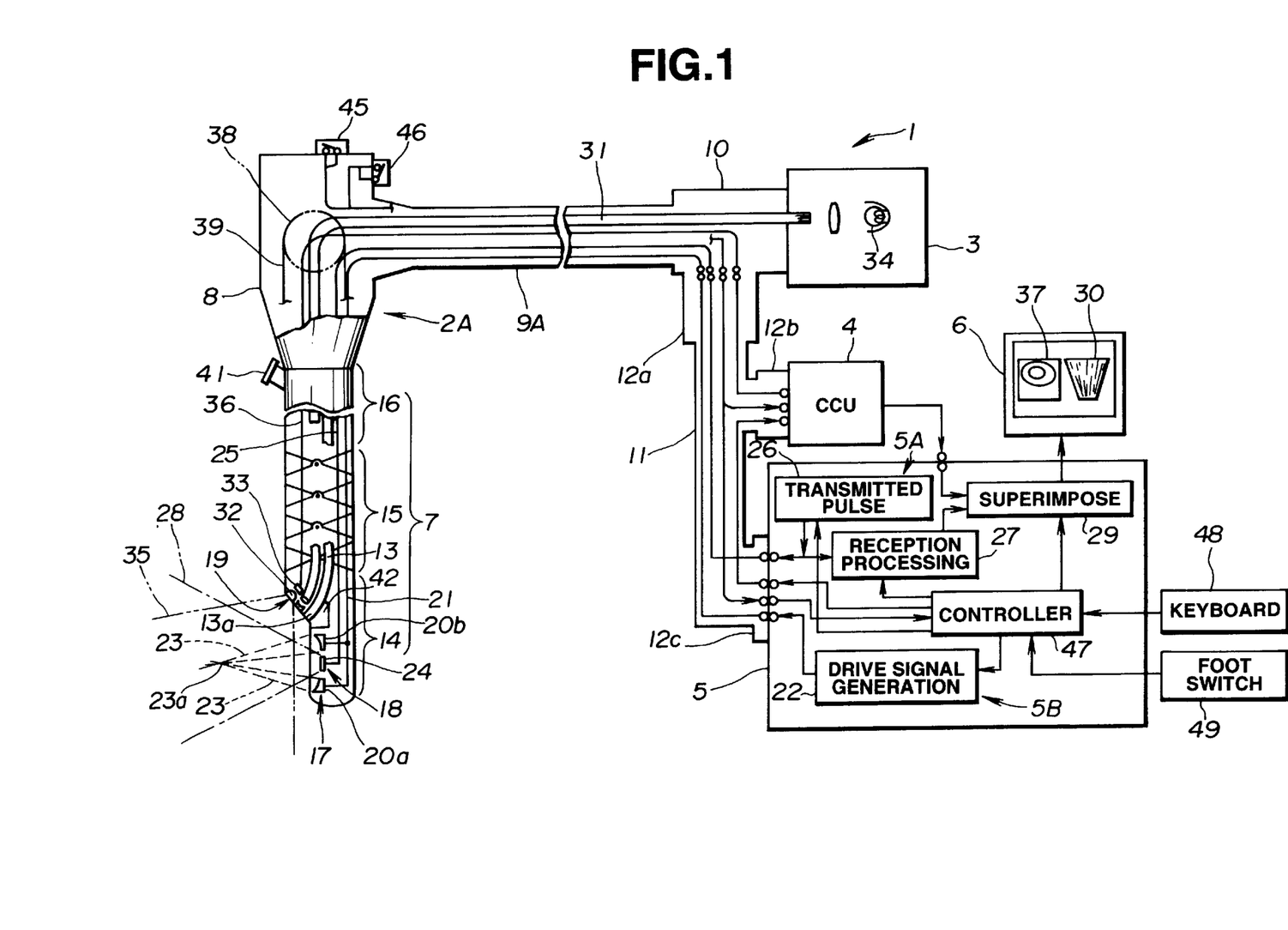
FIG. 1 is a diagram of the overall construction of an ultrasonic diagnosis and treatment system.

As shown in FIG. 1, an ultrasonic diagnosis and treatment system 1 of this embodiment has an ultrasonic probe 2A having, for example, the construction of an electronic endoscope, a light source unit 3 for supplying illumination light to the ultrasonic probe 2A, a camera control unit (CCU) 4 for performing signal processing for image pickup means incorporated in the ultrasonic probe 2A, an ultrasonic diagnosis/treatment circuit 5 incorporating an observation signal processing section 5A in which an ultrasonic image is formed, a treatment signal processing section 5B in which a treatment ultrasonic signal is formed, and a color monitor 6 for displaying an endoscopic image and an ultrasonic image by a video signal from the CCU 4 and a video signal from the observation signal processing section 5A.

The ultrasonic probe 2A has an inserted portion 7 formed as a thin tube to enable insertion into body cavities, a thicker operating portion 8 formed at the rear end of the inserted portion 7, gripped by an operator to perform inserting and curving operations, and a universal cable 9A extending from the operating portion 8. A light source connector 10 provided at an end of the universal cable 9A can be detachably connected to the light source unit 3. A signal connector 12a provided at one end of a signal cable 11 is connected to the light source connector 10, and a CCU connector 12b connected to the CCU 4 and an ultrasonic connector 12c connected to the ultrasonic diagnosis/treatment circuit 5 are connected to other end portions of the signal cable 11. The ultrasonic probe 2A, the CCU 4 and the ultrasonic diagnosis/treatment circuit 5 are connected through the signal cable 11.

The inserted portion 7 is formed of a hard extreme end section 14, a curving section 15 capable of being freely curved, a hard or flexible inserted tube section 16, which are successively formed from the extreme end side of the inserted portion 7. A channel 13, which is a lumen through which a guide needle or the like (described later below) is passed, is formed in the inserted portion. An opening 13a of the channel 13, ultrasonic treatment means 17, ultrasonic observation means 18 and optical observation means 9 are provided in the extreme end section 14.

The ultrasonic treatment means 17 is formed of treating ultrasonic vibrators 20a, 20b each formed so as to have, for example, a concave surface. These ultrasonic vibrators 20a, 20b form a pair of ultrasonic vibrators differing in curvature (R) from each other, are disposed in the extreme end section 14, and are connected to a drive signal generation circuit 22 in the ultrasonic diagnosis/treatment circuit 5 through a signal line 21 passing through the inserted portion 7 and other portions.

Each of the treating ultrasonic vibrators 20a, 20b emits ultrasonic waves by receiving a drive signal from the drive signal generation circuit 22 in the ultrasonic diagnosis/treatment circuit 5 through the signal line 21. By the effect of the concave surface configuration of the vibrators, the emitted ultrasonic waves form treating ultrasonic beams having a directionality represented by emission ranges 23 indicated by the broken lines in FIG. 1 to be converged at a convergent point 23a. At the convergence point 23a, the ultrasonic beams have a very large intensity, i.e., a high acoustic energy density. Accordingly, a treating operation can be performed in such a manner that a lesion tissue such as a tumor is set close to the convergence point 23a and, in this state, a drive signal is applied to the treating ultrasonic vibrators 20a, 20b to cauterize the lesion tissue by using high-density acoustic energy.

The ultrasonic observation means 18 is formed of, for example, a sector scan type observing ultrasonic vibrator 24 and is connected to a transmitted pulse generation circuit 26 and a reception processing circuit 27 forming the observation signal processing section 5A through a signal line 25 passed through the inserted portion 7 and other portions.

The observing ultrasonic vibrator 24 emits ultrasonic waves to the object tissue for sequentially a radial ultrasonic observation regions 28 indicated by the dot-dash lines in FIG. 1, as transmitted pulses from the transmitted pulse generation circuit 26 are applied to the observing ultrasonic vibrator 24. Ultrasonic waves reflected by the object tissue are received by the observing ultrasonic vibrator 24 and converted into an electrical signal. This ultrasonic echo signal is processed by the reception processing circuit 27 to be converted into a video signal corresponding to an ultrasonic image. The signal is thereafter supplied to the color monitor 6 through a superimposition circuit 29 to be displayed as an ultrasonic tomographic image 30.

The optical observation means 19 has illumination light emission means formed of an obliquely-forward-viewing optical system capable of emitting illumination light through a light guide 31, an illuminating lens and an illuminating window, and image pickup means including an objective lens 32 for forming an optical image of the object tissue illuminated with the illumination light and a charge coupled device (CCD) 33 disposed at the focal plane of the objective lens 32. The light guide 31 passes through the inserted portion 7 and other portions to extend to the light source connector 10. The light source connector 10 is connected to the light source unit 3 to enable illumination light generated by a lamp 34 and condensed by a lens to be incident upon an end surface of the light guide 31.

The illumination light from the light source unit 3 is transmitted to the extreme end section 14 through the light guide 31, and is led from a fore end surface of the light guide to a lens at the illuminating window to be emitted obliquely forward. The range of illumination with this illumination light emitted obliquely forward coincides generally with the observation range 35 of the objective lens 32 indicated by the double dot-dash-line in FIG. 1. An optical image of the object tissue is imaged on the image pickup surface of the CCD 33 by the objective lens 32. The CCD 33 is connected to a video signal processing section in the CCU 4 by a signal line 36. A picked-up image signal from the CCD 33 is converted into a video signal by the video signal processing section and is thereafter input to the color monitor 6 through the superimposition circuit 29 to be displayed as endoscopic image 37 together with ultrasonic tomographic image 30.

In the curving section 15, a multiplicity of curving pieces are connected so as to be rotatable relative to each other. A curving wire 39 is passed through the inserted portion 7 including the curving section 15. One end of the curving wire 39 is connected to the extreme end section 14 and the other end is connected to a pulley 38 provided in the operating portion 8. In the curving section 15 thus constructed in the same manner as the curving section used in the ordinary endoscope, the curving pieces are rotated by pulling and loosening the curving wire 39 through the operation of rotating a curving knob (not shown) connected to the pulley 38, whereby the curving section 15 can be curved in four directions, i.e., upward, downward, leftward and rightward directions, or in two directions, i.e., upward and downward directions or leftward and rightward directions. By this curving movement of the curving section 15, the extreme end section 14 can be freely swung in any direction to set the ultrasonic treatment means 17, the ultrasonic observation means 18, the optical observation means 19 and the channel opening 13a in a desired direction.

A guide inlet 41 communicating with the channel 13 is formed in the vicinity of the base end of the inserted portion 7. A guide needle or the like described below can be led into the channel 13 through the inlet 41, and can be passed through the channel 13 to project outward through the channel opening 13a. A raising base 42 for raising in a predetermined direction an extreme end portion of the guide needle or the like passed through the channel 13 is provided in the vicinity of the channel opening 13a.

Image control buttons (or image control switches) 45, 46 for a change control or the like for changing freezing or display of endoscopic images are provided on the operating portion 8 at rear end positions. The image control buttons 45, 46 are connected to the CCU 4 and a controller 47 provided in the ultrasonic diagnosis/treatment circuit 5 to supply designation signals input by the image control buttons 45, 46 to the CCU 4 and the controller 47.

A keyboard 48 and a foot switch 49 are connected to the controller 47. A period of time for treatment using the ultrasonic treatment means 17 can be set through the keyboard 48 and information on a patient's chart or the like can also be input through the keyboard 48. An instruction to start or stop a treatment with the ultrasonic treatment means 17 can be input by operating the foot switch 49.

The controller 47 is connected to the transmitting circuit 26 and other circuits in the ultrasonic diagnosis/treatment circuit 5 and is adapted to perform various kinds of control and to change conditions for ultrasonic wave transmission of ultrasonic images, conditions for signal processing of received signals, ultrasonic treatment output conditions and the like. The controller 47 is also connected to the CCU 4 to control the CCU 4 from the keyboard 48.

Figure 2:
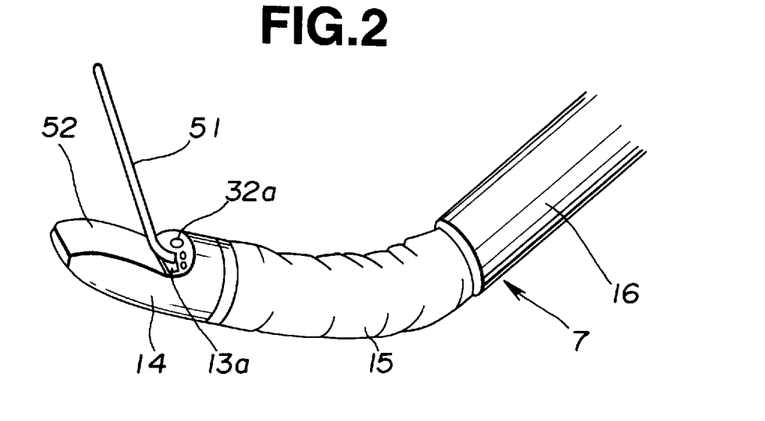
FIG. 2 is a perspective view of the construction on the extreme end side of an ultrasonic probe for emitting diagnosis ultrasonic waves and treating ultrasonic waves.

FIG. 2 shows the external appearance and construction of the inserted portion 7 at the extreme end side. In the inserted portion 7, the extreme end section 14, the curving section 15 and the inserted tube section 16 are formed from the extreme end side continuously one with another. An extreme end of a guide needle 51 punctures a treatment target part to guide to the treatment target part an operating instrument or the like inserted into a lumen of the guide needle 51. In the extreme end section 14, the guide needle 51 is projected out of the channel opening 13a provided in the vicinity of the observation window 32a of the optical observation means 19.

Figure 3:
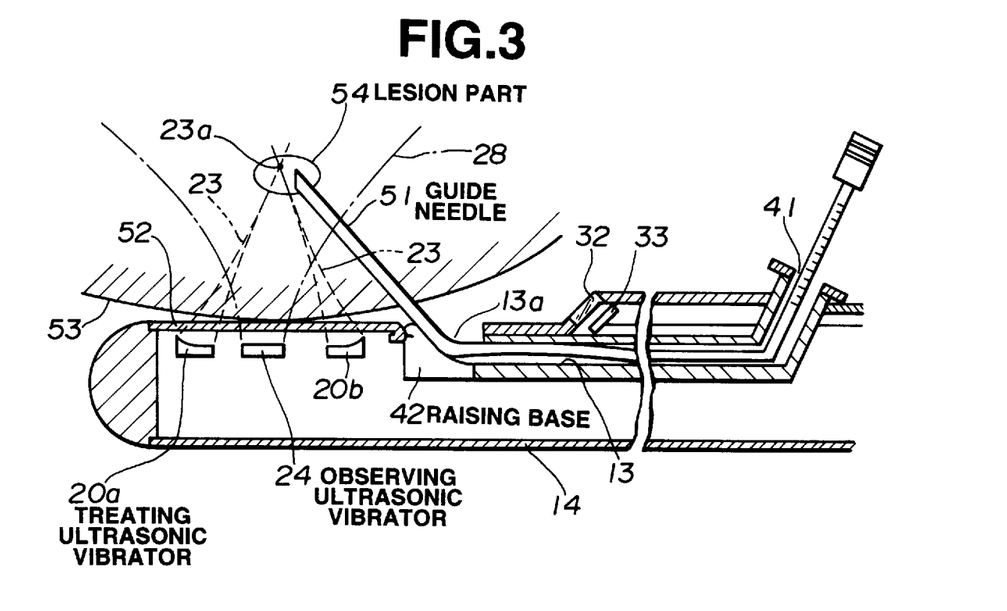
FIG. 3 is a schematic cross-sectional view of the construction on the extreme end side of the ultrasonic probe, showing a state when diagnosis and treatment are made.

FIG. 3 is a cross-sectional view of the extreme end section 14 and other portions in the vicinity of the extreme end section 14 in a state where the ultrasonic probe 2A is inserted to a position in the vicinity of a treatment target part and where the guide needle 51 is inserted and passed to puncture the treatment object portion.

To make diagnosis and treatment by using the ultrasonic probe 2A constructed as described above, the inserted portion 7 of the ultrasonic probe 2A is inserted into a body cavity, internal regions of the body cavity are observed by the optical observation means 19 including the CCD 33, and an observing surface 52 of the extreme end section 14 along which the ultrasonic vibrators 20a, 20b, and 24 are disposed are brought into contact with an organic tissue 53 to observe and diagnose a lesion part 54 such as cancer and other regions in the vicinity of the lesion part 54 by the ultrasonic observation means 18 including the observing ultrasonic vibrator 24, as shown in FIG. 3. While the lesion part 54 and the vicinal regions are being observed, the convergent point 23a of the treating ultrasonic beams from the treating ultrasonic vibrators 20a, 20b is positioned on the lesion part 54 and a treating operation is performed by cauterizing the lesion part 54 at a high temperature by the ultrasonic treatment means 17 including the treating ultrasonic vibrators 20a, 20b.

In this embodiment, the guide needle 51 is inserted through the guide inlet 41 of the ultrasonic probe 2A to be guided to the treatment target part, i.e., lesion part 54 through the channel 13, and the operating instrument or the like can be guided to the lesion part 54 through the lumen of the guide needle 51, thereby enabling a treatment or operation other than the ultrasonic treatment to be made by the operation means including the guide needle and the operating instrument.

The raising base 42 provided in the ultrasonic probe extreme end section 14 has a surface inclined at a predetermined angle and is fixed in the vicinity of the channel opening 13a. Therefore, when the guide needle is inserted, the raising base 42 serves as a guide for operation means, and the guide needle 51 raised by the raising base 42 projects at a certain angle previously set and in such a direction as to extend toward the convergent point 23a of the treating ultrasonic beams output from the treating ultrasonic vibrators 20a, 20b. Consequently, as the guide needle 51 is passed through the channel 13, it is raised on the raising base 42 to project in the ultrasonic observation/treatment direction and to be led to the treatment object lesion part 54 located in front of the guide needle 51 in the projecting direction determined by the raising base 42.

Figure 4:
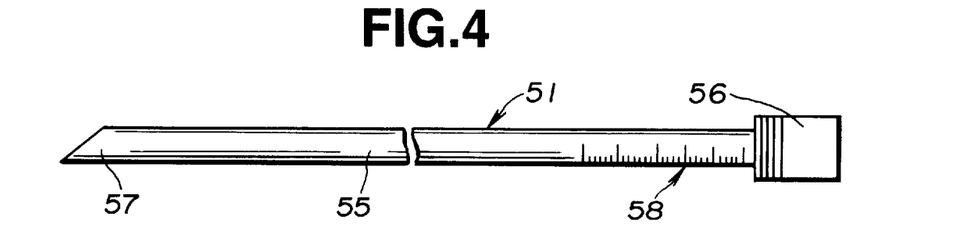
FIG. 4 is a diagram of the construction of a guide groove passed through the ultrasonic probe.

As shown in FIG. 4, the guide needle 51 has a guide probe 55 which is hollow and flexible and which serves as a guide tube, and a connector portion 56 formed in connection with a base end portion of the guide probe 55. The guide probe 55 is formed of a tubular member having a lumen through which an operating instrument or the like can be inserted and led to the extreme end. Also, an acute portion is formed at the extreme end of the guide probe 55 so as to be able to puncture an organic tissue. A scale 58 is provided on an outer surface portion of the guide probe 55 at the base end side as an insertion amount setting means which indicates the amount of insertion of the guide needle 51 to make it possible to confirm and set the amount of insertion.

That is, the raising base 42 that serves as a guide for operation means of the ultrasonic probe 2A is fixed at the predetermined angle and the guide needle 51 passed through the channel 13 projects at the fixed angle, so that when the guide needle 51 is inserted into the channel 13 by a predetermined amount while observing the scale 58 of the guide needle 51, the position of the extreme end 57 of the guide probe 55 is definitely determined according to the position of the scale 58.

Figure 5:
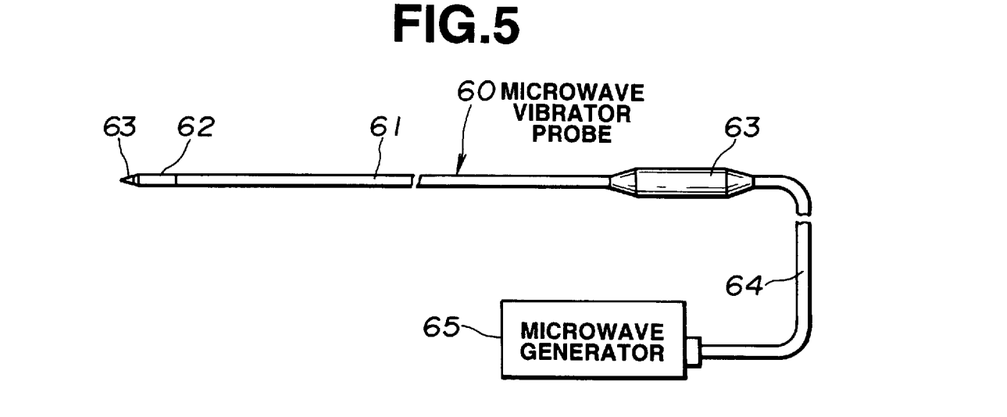
FIG. 5 is a diagram of the construction of a microwave treatment apparatus having a microwave vibrator probe inserted into a lumen of the guide needle.
Figure 6:
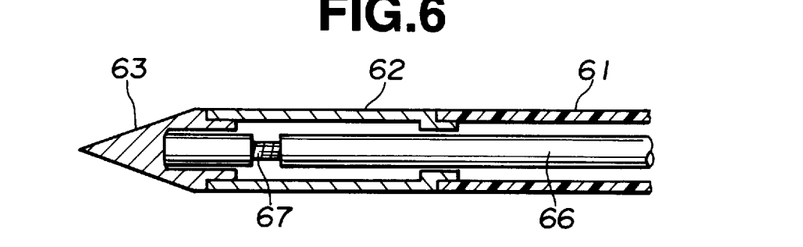
FIG. 6 is a cross-sectional view of the construction of an extreme end portion of the microwave vibrator probe of FIG. 5, taken along a longitudinal axis thereof.

FIG. 5 shows the overall construction of a microwave treatment apparatus having a microwave vibrator probe (MW probe) inserted in the guide needle 51 and used in combination with the guide needle 51. FIG. 6 is a cross-sectional view of a portion of the microwave vibrator probe shown in FIG. 5 in the vicinity of the extreme end.

The microwave vibrator probe 60 is constructed in such a manner that an extreme end portion 62 is connected to a fore end of a hard inserted portion 61, and a grip portion 63 is connected to a base end of the inserted portion 61. A conical tip 63 is provided at the extreme end of the extreme end portion 62 of the microwave vibrator probe 60, and microwaves (MW electromagnetic waves) are emitted from the extreme end portion 62 in the vicinity of the tip 63. The microwave vibrator probe 60 is connected to a microwave generator 65 through a connection cord extending from the rear end of the grip portion 63 and is thereby supplied with microwaves from the microwave generator 65.

In the microwave vibrator probe 60, as shown in FIG. 6, a coaxial cable 66 for transmitting microwaves is inserted into the extreme end portion 62, in which a microwave antenna 67 formed of slits is provided integrally with the coaxial cable 66 in the vicinity of the extreme end of the same.

Each of the extreme end portion 62 and the tip 63 of the microwave vibrator probe is formed of a material having a small dielectric constant to avoid obstruction to the radiation of microwaves. The tip 63 is formed into a conical shape for easily puncturing tissues in body cavities.

To diagnose and treat a tissue in a body cavity by using the ultrasonic probe 2A of this embodiment, the inserted portion 7 of the ultrasonic probe 2A is first inserted into the body cavity, and an optical observation image and an ultrasonic observation image of a treatment target part are obtained by the optical observation means 19 including the CCD 33 and the ultrasonic observation means 18 including the observing ultrasonic vibrator 24 to display ultrasonic tomographic image 30 and endoscopic image 37 on the monitor 6. A lesion part 54 and other regions in the vicinity of lesion part 54 are observed through these images.

At this time, optical information on an optical image of the interior of the body cavity obtained through the objective lens 32 is converted into an electrical picked-up image signal by the CCD 33, and the obtained picked-up image signal is processed by the CCU 4 to form a video signal of the endoscopic image. The endoscopic image 37 is displayed on the monitor 6 to observe the interior of the body cavity in the vicinity of the ultrasonic probe extreme end section 14.

Also, ultrasonic waves are transmitted and received by the observing ultrasonic probe vibrator 24 to obtain an ultrasonic signal for ultrasonic probe observation in the vicinity of the lesion part 54 such as cancer. The received ultrasonic signal is processed in the observation signal processing section 5A to form a video signal of the ultrasonic tomographic image. The ultrasonic tomographic image 30 is displayed on the monitor 6 to observe the treatment target part, i.e., the lesion part 54 such as cancer and other regions in the vicinity of the lesion part 54. At this time, the curving section 15 of the ultrasonic probe 15 is curved to swing the extreme end section 14 by desired angles so that the observing surface of the extreme end section 14 is brought into contact with the organic tissue 53 of the treatment target part to observe the same.

Thereafter, while the lesion part 54 and other regions in the vicinity of the lesion part 54 are being observed by the ultrasonic observation means 18 as described above, the convergent point (focal point) 23a of treating ultrasonic beams emitted from the pair of treating ultrasonic vibrators 20a, 20b differring in curvature from each other is positioned on the lesion part 54, and strong treating ultrasonic beams are emitted from the treating ultrasonic vibrators 20a, 20b to cauterize the lesion tissue at a high temperature by the increased density of acoustic energy of the ultrasonic waves at the convergent point, thus performing an ultrasonic treating operation.

Next, the guide needle 51 is inserted into the channel 13 of the ultrasonic probe 2A while the above-mentioned diagnostic images are being observed on the monitor 6. As the guide needle 51 is inserted, its extreme end portion projects in a certain direction from the channel opening 13a, since the raising base 42 provided in the ultrasonic probe extreme end section 14 to serve as a guide for operation means is fixed at a predetermined angle. The guide needle 51 is inserted by a predetermined amount while reading the indication on the scale 58 of the guide probe 55, thereby definitely determining the position of the extreme end 57 of the guide needle 51. Accordingly, the extreme end 57 of the guide needle 51 can be positioned at the convergent point 23a of the treating ultrasonic beams output from the treating ultrasonic vibrators 20a, 20b or a position in the vicinity of the convergent point 23a, i.e., at the lesion part 54. In this manner, the extreme end 57 of the guide probe 55 of the guide needle 51 is made to reach the lesion part 54.

Figure 7:
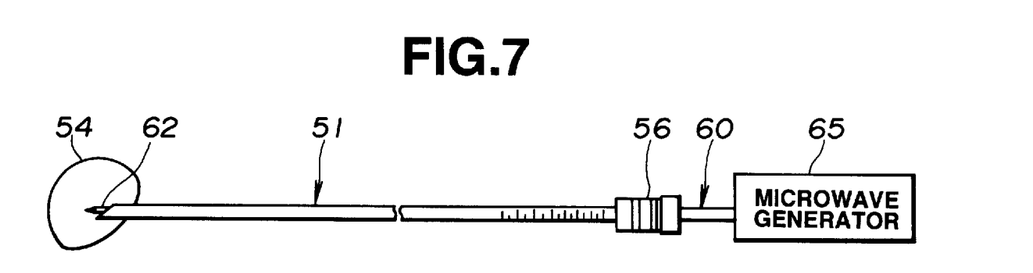
FIG. 7 is a diagram of operation in a state where the microwave vibrator probe is passed through the lumen of the guide groove to puncture a treated part.

Subsequently, as shown in FIG. 7, the microwave vibrator probe 60 as a treating probe is inserted into the lumen of the guide needle 51 from the connector portion 56 on the operator side, and the probe extreme end portion 62 is projected from the extreme end of the guide needle 51 to puncture the lesion part 54. In the arrangement of this embodiment, as described above, the treating operation means including the guide needle 51 and the microwave vibrator probe 60 are inserted into the body cavity through the channel 13 of the ultrasonic probe 2A to enable the microwave vibrator probe 60 to reach the lesion part 54 through the guide needle 51. Microwaves having treating energy are supplied from the microwave generator 65 to the microwave vibrator probe 60, and MW electromagnetic waves are output from the probe extreme end portion 62 to heat, cauterize and solidify the lesion part 54, thus performing a treating operation using microwaves.

When a treatment with ultrasonic waves is made by the ultrasonic treatment means, the denaturation of protein of a tissue, for example, caused by casterization is observed through the ultrasonic diagnostic image obtained by the ultrasonic observation means, and the treated part is irradiated with strong treating ultrasonic waves while observing the protein denaturation, until the protein denaturation progresses to such an extent that cancerous cells die. At this time, the irradiation of treating ultrasonic waves is performed while confirming the state of the treating operation on the ultrasonic diagnostic image, and the irradiation is stopped when the target part is completely treated. In this embodiment, a treating operation using microwaves can be performed simultaneously with this ultrasonic treatment, thus making it possible to efficiently treat the lesion part.

In this embodiment, as described above, the ultrasonic probe 2A having the observing ultrasonic vibrator and the treating ultrasonic vibrators can be inserted into a desired part in a body cavity such as an upper digestive tube, a lower digestive tube, the thoracic cavity, the abdominal cavity, or a cerebral ventricle, and a treatment with ultrasonic waves can be made while a lesion part such as cancer is diagnosed in an ultrasonic diagnosis manner. Moreover, raising base 42 used as a guide for operation means is provided in ultrasonic probe 2A to enable the operation means including guide needle 51 and microwave vibrator probe 60 to be guided to a predetermined position and to reach a lesion part. It is therefore possible to perform an additional treatment in association with the ultrasonic treatment.

The effect of treating the diseased part can be improved because treatment can be made by using both ultrasonic energy and microwave energy as described above. Also, the position of lesion parts can easily be confirmed because the position of the extreme end of the guide needle inserted into a body cavity can be definitely determined by virtue of the guide for operation means.

Figure 8:
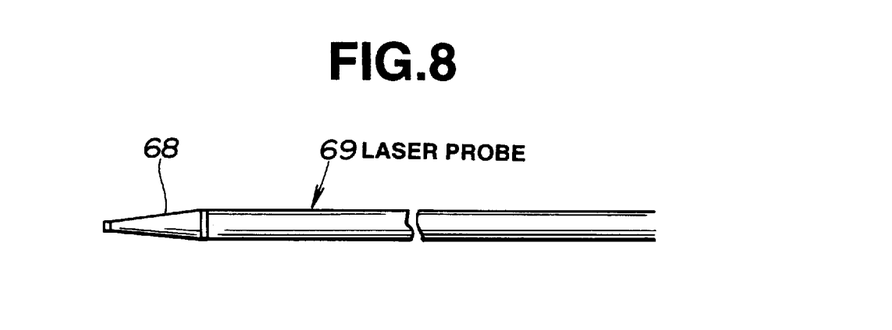
FIG. 8 is a diagram showing the construction of an extreme end portion of a laser probe used as operation means passed through the lumen of the guide groove.

The embodiment has been described as an example of an arrangement in which the guide needle, and the microwave vibrator probe are used as operation means made to reach a lesion part through the ultrasonic probe, and the microwave vibrator probe is inserted into the guide needle 51 to treat the lesion part. However, the present invention is not limited to this, and a laser probe 69 having a pointed contact tip 68 at its extreme end as shown in FIG. 8 may be applied as a treating probe in a similar manner. If such a laser probe 69 is used, treating laser light is supplied as treating energy to the laser probe 69 by a laser unit (not shown) connected to the probe and is output to a lesion part by the laser probe 69 to make a laser cauterization treatment.

A suction probe formed of a very thin probe and adapted to draw tumors with an ultrasonic sucking device or the like can also be applied in a similar manner.

As a treating probe, a heating probe may also be applied which is formed of a heat probe having at its extreme end a heating means such as a thermistor for heating and cauterizing a lesion part such as a tumor.

A cryotube may also be applied which has a flexible adiabatic pipe passage and which supplies a cooling medium such as nitrogen to the pipe passage to freeze-treat a lesion part around its puncturing extreme end portion.

Further, the arrangement may be such that the vibrator probe 60 shown in FIGS. 5 to 7 is constructed as a high frequency (HF) probe (high frequency current probe), and an operation of causing a high frequency current through a lesion part in the vicinity of the probe tip by power supplied from an HF power source to solidify and evaporate the lesion part. In such a case, the HF probe may be of a bipolar type or a monopolar type used in combination with an extracorporeal mated electrode.

The arrangement may alternatively be such that the vibrator probe 60 is constructed as a radio frequency (RF) probe (radio frequency electromagnetic wave probe) and is used in combination with an extracorporeal mated electrode to constitute a heating means, and this means is combined with the ultrasonic treatment to heat, cauterize and solidify a lesion part by RF electromagnetic waves.

According to this embodiment, as described above, a treating probe provided as an operation means is inserted into a desired region in a body cavity along with an ultrasonic probe for diagnosis and treatment to make both a treatment with ultrasonic waves and a different operation by an operation means, thus making it possible to treat the diseased part more efficiently and effectively.

FIGS. 9 through 13 illustrate the second embodiment of the present invention.

In this embodiment, the construction of an ultrasonic probe having diagnosing and treating ultrasonic vibrators is applied as a thin tube inserted for diagnosis and treatment in body cavities to an ultrasonic probe for use in the abdominal cavity, which is inserted in the abdominal cavity through a guide tube such as a trocar.

Figure 9:
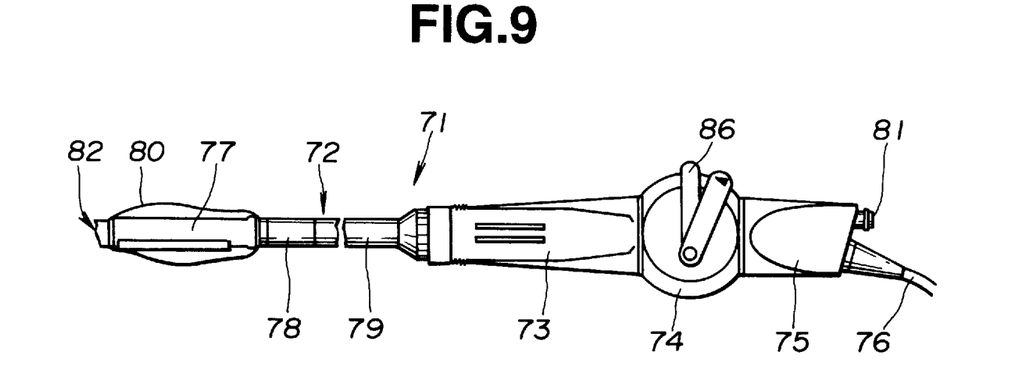
FIG. 9 is a diagram of the construction of an in-abdominal-cavity ultrasonic probe which emits diagnosing and treating ultrasonic waves.

As illustrated in FIG. 9, an ultrasonic probe 71 used in an ultrasonic diagnosis/treatment system in accordance with this embodiment has an inserted portion 72 in the form of a thin tube, a thick first grip portion 73 which is formed continuously with the rear end of the inserted portion 72 and which is gripped by an operator, an operating portion 74 formed on the rear end side of the first grip portion 73 and which is used for inserting and curving operations, a second grip portion 75 formed on the rear end side of the operating portion 74, and a connection cable 76 extending from the second grip portion 75 and connected to an ultrasonic diagnosis/treatment circuit and other components (not shown).

The ultrasonic diagnosis/treatment circuit and other components are arranged in the same manner as in the first embodiment and will not be specially described.

The inserted portion 72 of the ultrasonic probe is formed by successively connecting, from the extreme end side, a hard extreme end section 77, a curving section 78 capable of being freely curved, and an inserted tube 79 formed of a hard tubular member.

In the extreme end section 77, an ultrasonic vibrator is incorporated, as described below, and a balloon 80 is provided which can be attached so as to cover a peripheral surface of the extreme end section 77. In the balloon 80 is enclosed an ultrasonic wave transmitting medium for providing an acoustic coupling function for acoustic impedance matching between the ultrasonic probe and organic tissues. An introducing tubular passage (not shown) which communicates with the interior of the balloon 80 is formed in the ultrasonic probe 71, and an injection port 81 which communicates with a base end portion of the introducing tubular passage is provided in the second grip portion 75. The ultrasonic wave transmitting medium is injected through the injection port 81 to be supplied into the balloon 80 through the introducing tubular passage.

Figure 10:
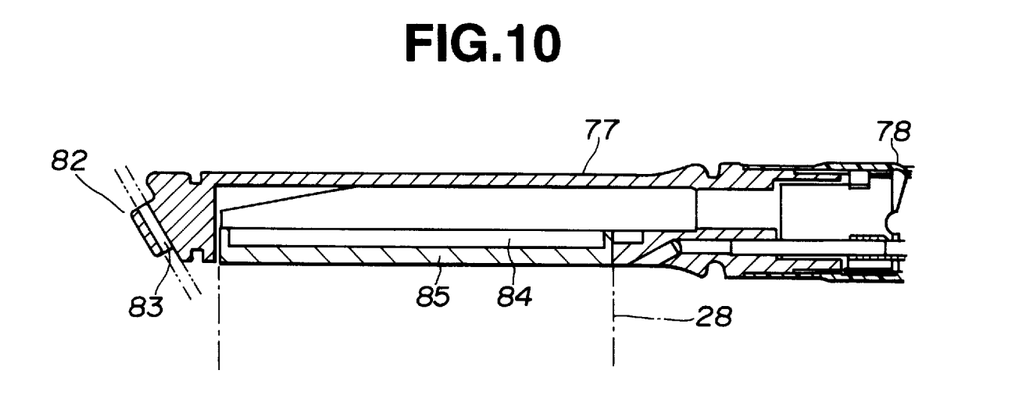
FIG. 10 is a cross-sectional view of the construction of an extreme end portion of the ultrasonic probe shown in FIG. 9.

On the extreme end of the ultrasonic probe extreme end section 77, an operation means guide 82 is provided which has a fitting groove or an insertion hole into which a guide needle or the like can be inserted, and which is adapted to guide operating instruments or the like including a guide needle. In the operation means guide 82, as shown in FIG. 10, a guide groove 83 having a predetermined angle with respect to the direction along a longitudinal axis of the ultrasonic probe is formed as a fitting groove into which a guide groove or a treating probe used as a puncturing probe is fitted and inserted. The guide groove 83 enables an operating instrument or the like to be guided into an ultrasonic observation region 28 in the direction at the predetermined angle.

In the ultrasonic probe extreme end section 77, a linear array type ultrasonic vibrator 84 for ultrasonic observation is provided, and an acoustic matching layer 85 is provided on the ultrasonic vibration emission side of the linear array type ultrasonic vibrator 84 to enable ultrasonic waves for observation to be emitted into the ultrasonic observation region 28. A treating ultrasonic vibrator (not shown) is also provided in the ultrasonic probe extreme end section 77 to emit treating ultrasonic waves, as in the first embodiment.

As shown in FIG. 9, a curving operation knob 86 for operating the curving section 78 for curving movement is provided on the operating portion 74, and is connected to a curving mechanism (not shown) which is substantially the same as that in the first embodiment.

Figure 11:
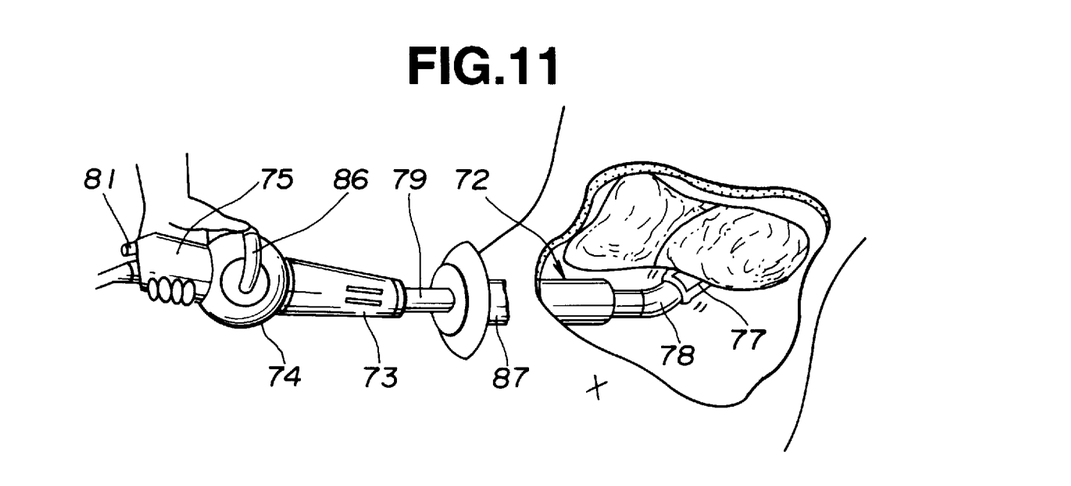
FIG. 11 is a diagram of operation in a state where the ultrasonic probe is inserted into a body cavity.

To make diagnosis and treatment by using the abdominal cavity ultrasonic probe 71 of this embodiment, the first grip portion 73 or the second grip portion 75 is first gripped to insert through a trocar 87 or the like the extreme end section 77 of the inserted portion 72 into a target part in the abdominal cavity inflated by pneumoperitoneum, as illustrated in FIG. 11. Thereafter, the curving section 78 is curved by operating the curving operation knob 86 of the operating portion 74. The ultrasonic wave emitting surface of the linear array type ultrasonic vibrator 84 incorporated in the extreme end section 77 is thereby set in contact with the surface of the treatment target organ. In this state, ultrasonic waves for observation are transmitted and received to obtain an ultrasonic observation image of the treatment target part, and an ultrasonic tomographic image is displayed on the monitor screen to observe and diagnose the lesion part and other regions in the vicinity of the lesion part.

When an organ in the abdominal cavity is diagnosed and treated in this manner, an optical viewing tube or the like (not shown) is inserted into the abdominal cavity separately of the ultrasonic probe to perform an optical observation.

Figure 12:
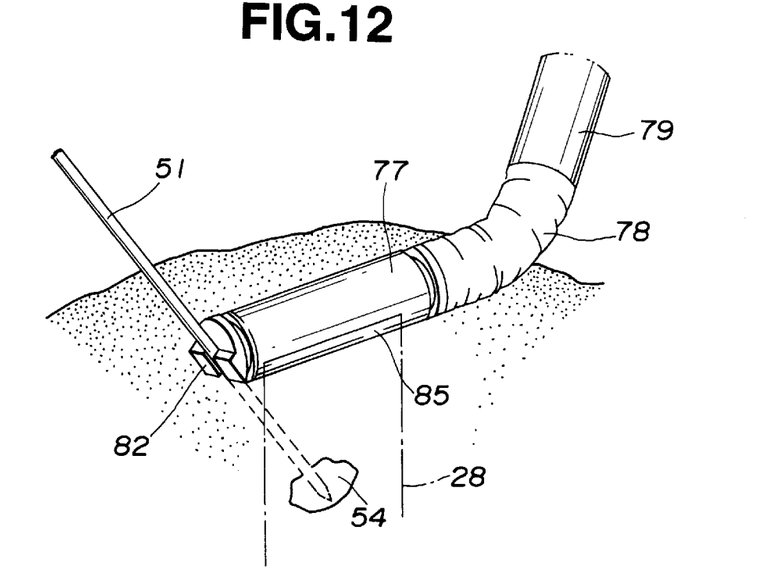
FIG. 12 is a diagram of operation in a state where operation means is guided to reach a treated part by the operation means guide provided at the extreme end of the ultrasonic probe.

FIG. 12 shows a state in the vicinity of the ultrasonic probe extreme end at the time of ultrasonic diagnosis and treatment. As described above, the extreme end section 77 of the ultrasonic probe is brought into contact with the treatment object organ and ultrasonic waves are transmitted to the ultrasonic observation region 28 to obtain an ultrasonic tomographic image. Also, the lesion part 54 can be treated with ultrasonic waves by emitting treating ultrasonic waves from the treating ultrasonic vibrator, while ultrasonic diagnosis is being made, as in the first embodiment, although such treatment is not illustrated.

While an ultrasonic diagnosis and an optical observation are being made, a guide needle 51 is inserted into the guide groove 83 of the operation means guide 82, and the operation means guide 82 enables the guide needle 51 to reach the lesion part 54. Thereafter, a temperature detecting probe 90 shown in FIG. 13, having a temperature sensor 89 such as a thermocouple, is inserted into the lumen of the guide needle 51 to stick the probe end into the lesion part 54.

In this embodiment, a temperature detecting probe which is intracorporeal information detection means is used as an operation means to monitor the temperature of a treated part, thereby making it possible to grasp the state of treatment process and to control a treating energy output such as ultrasonic waves, microwaves or laser. The configuration of a means for monitoring and controlling such a treating energy output will be described with reference to FIG. 13.

Figure 13:
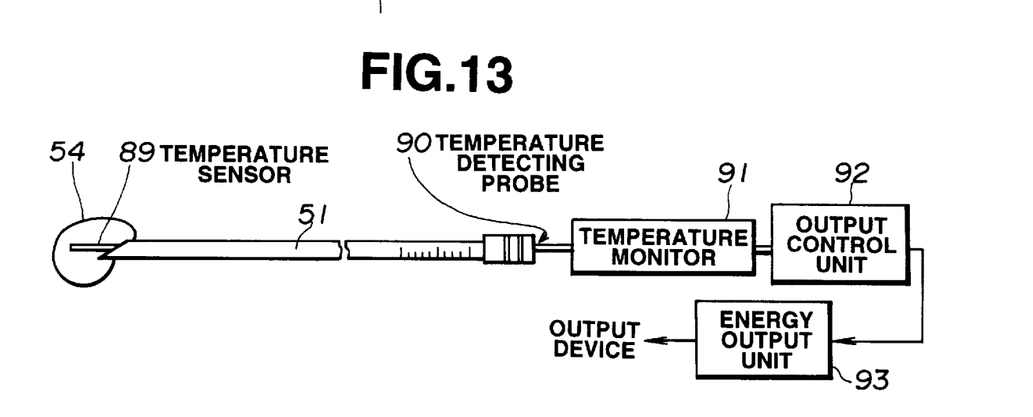
FIG. 13 is a diagram of the construction of output control means having a temperature detecting probe provided as a means for monitoring the condition of a treated part, showing an operation in a state where the temperature detecting probe is passed through the lumen of the guide needle to puncture the treated part.

The temperature detecting probe 90 has at its extreme end a temperature sensor 89 such as a thermocouple for detecting temperature. The temperature detecting probe 90 can be passed through the lumen of the guide needle 51 and can be led through the guide needle 51 to the lesion part 54, i.e., the treated part, to puncture the lesion part 54 to detect the temperature of the treated part. The temperature monitor 91 is connected to the temperature detecting probe 90, and a signal representing the temperature value of the treated part detected through the probe extreme end section is output from the temperature monitor 91.

To the temperature monitor 91, an output control unit 92 and an energy output unit 93 for outputting treating energy are successively connected. An output control signal according to the detected temperature value obtained as an output from the temperature monitor 91 is fed back from the output control unit 92 to the energy output unit 93 to control the treating energy output from the energy output unit 93 to an output device such as an ultrasonic vibrator, a microwave vibrator probe or a laser probe.

During treatment with ultrasonic waves or microwaves, the temperature of the treated part varies depending upon the amount of ultrasonic waves or the like output as treating energy. In such a situation, it is possible to grasp the treated condition by detecting the temperature of the treated part.

The temperature sensor 89 of the temperature detecting probe 90 punctures the lesion part 54 to detect the temperature during treatment, and the detected temperature value is sent to the output control unit 92 through the temperature monitor 91. Thus, the temperature during treatment by emitting ultrasonic waves, microwaves, laser light or the like from an output device is monitored and the output control unit 92 outputs the output control signal to control the energy output unit 93. For example, the control is such that the output from the energy output unit 93, i.e., treating energy such as ultrasonic waves, microwaves or laser light, is reduced if the temperature of the treated part is greater than a predetermined value, or the output from the energy output unit 93 is increased if the temperature of the treated part is less than the predetermined value.

The means for monitoring the state of treated parts is not limited to the above-described temperature detecting probe 90. Alternatively, a sound pressure detecting probe 95 such as that shown in FIG. 14 may be used. The construction and function of an output monitoring control means for controlling a treating ultrasonic wave output by monitoring the sound pressure from a treated part will be described with reference to FIG. 14.

Figure 14:
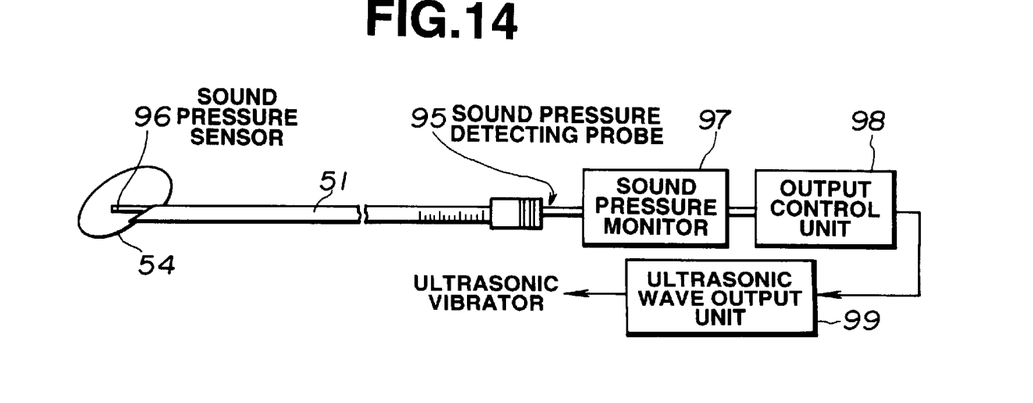
FIG. 14 is a diagram of the construction of output control means having a sound pressure detecting probe provided as a means for monitoring the condition of a treated part, showing an operation in a state where the sound pressure detecting probe is passed through the lumen of the guide needle to puncture the treated part.

A sound pressure sensor 96 for detecting sound pressure is provided at the extreme end of the sound pressure detecting probe 95. The sound pressure detecting probe 95 can be passed through the lumen of the guide needle 51 and can be led through the guide needle 51 to the lesion part 54, i.e., the treated part to puncture the lesion part 54 to detect the sound pressure at the treated part. A sound pressure monitor 97 is connected to the sound pressure detecting probe 95, and a signal representing the sound pressure value of the treated part detected through the probe extreme end section is output from the sound pressure monitor 97. To the sound pressure monitor 97, an output control unit 98 and an ultrasonic wave output unit 99 are successively connected. An output control signal according to the detected sound pressure value obtained as an output from the sound pressure monitor 97 is fed back from the output control unit 98 to the ultrasonic wave output unit 99 to control the treating ultrasonic wave output from the ultrasonic wave output unit 99 to the ultrasonic vibrator.

During treatment with ultrasonic waves, sound pressure is detected by puncturing the lesion part 54 with the sound pressure sensor 96 of the sound pressure detecting probe 95, and the detected sound pressure value is sent to the output control unit 98 through the sound pressure monitor 97. In this manner, the ultrasonic wave irradiation output value is monitored by detecting sound pressure during treatment, and the output control unit 98 outputs the output control signal to control the ultrasonic wave output unit 99. Thus, the state of the treatment process using ultrasonic waves is grasped and the ultrasonic wave irradiation output is controlled.

As described above, the temperature detecting probe or the sound pressure detecting probe is led to a treated part to make it possible to monitor the condition of the treated part in a real time manner by detecting the temperature or sound pressure of the lesion part during treatment and to perform an output control of the operation means according to the condition of the treated part. Consequently, it is possible to improve the reliability of treating operations and the safety for the living body.

The relationship between the object regions of an ultrasonic treating operation and other operation will now be described.

Figure 15:
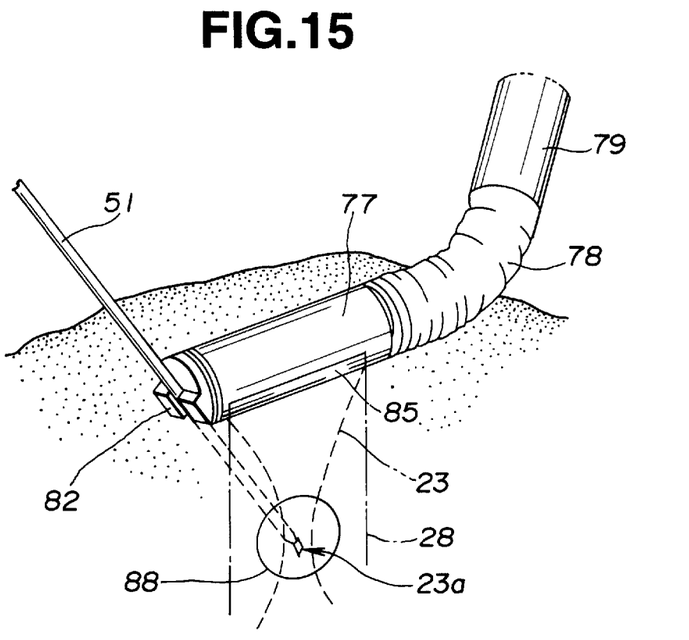
FIG. 15 is a diagram of an operation showing regions of a treating operation using converged ultrasonic waves and another kind of operation under the guidance of ultrasonic diagnosis using the ultrasonic probe.

FIG. 15 shows a region treated by a treatment with converged ultrasonic waves from the ultrasonic probe under the guidance of ultrasonic diagnosis, and regions treated by other operations.

The extreme end section 77 of the ultrasonic probe is placed on a somatic surface of a treated part, and ultrasonic waves are emitted from the treating ultrasonic vibrator. The part at the convergent point 23a is treated by being cauterized by converged ultrasonic waves radiated from the extreme end section 77. On the other hand, the guide needle 51 or one of probes for various kinds of operations is led to and punctures the part at the convergent point 23a through the operation means guide 82 that serves as a puncturing guide.

The region treated by the probes for various kinds of operations is not limited to the region treated with converged ultrasonic waves (indicated at 23a in FIG. 15) but it covers a larger region therearound, as indicated at 88 in FIG. 15. Accordingly, treatments of other operations are used along with a treatment with ultrasonic waves in a limited region in order that treatments can be made throughout a larger region.

Figure 16:
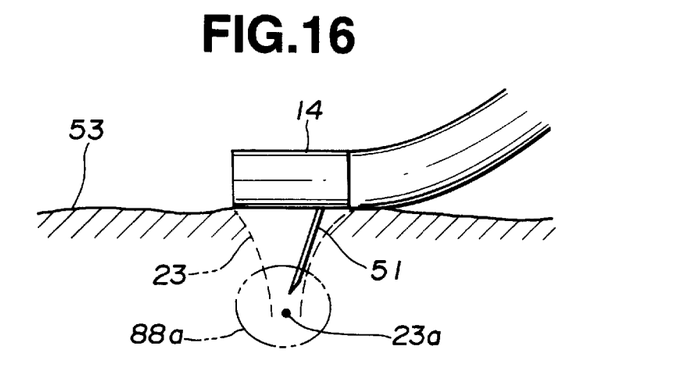
FIG. 16 is a diagram showing an example of the relationship between object regions of a treating operation using converged ultrasonic waves and another kind of operation.

As described above, the regions treated by other operations are not limited to the region coinciding with the region treated with converged ultrasonic waves, and, as shown in FIG. 16, other operations may have, as a treatment object, a larger vicinal region 88a including the region 23a treated with converged ultrasonic waves in organic tissue 53. The guide needle 51 or the like may puncture such a region to lead each of the probes for various kinds of operations thereinto to make an auxiliary treatment by the treatment other than the ultrasonic treatment as well as to assist the ultrasonic treatment by sound pressure detection or temperature detection. For example, such a method may be applied to a treatment in which a part of a lesion tissue is treated by being strongly cauterized by converged ultrasonic waves while parts of possibly desirous tissues therearound are treated by being weakly cauterized.

Figure 17:
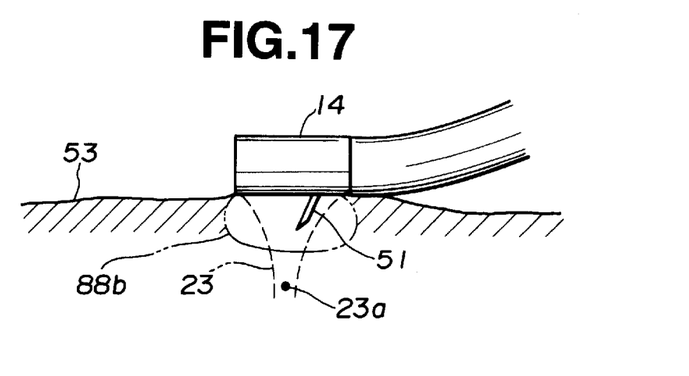
FIG. 17 is a diagram showing another example of the relationship between object regions of a treating operation using converged ultrasonic waves and another kind of operation.

It is also possible that, as shown in FIG. 17, an internal portion of organic tissue 53 is treated with converged ultrasonic waves 23 while a tissue surface in another portion shallower than the region 23a treated by the converged ultrasonic waves 23 or a portion in the vicinity thereof is set as a treated region 88b which is the object of a different operation. In this case, the guide needle 51 or each of the probes for various kinds of operations may puncture the object region or each of the probes for various kinds of operations may be brought into contact with the tissue surface to enable the region shallower than the region treated with ultrasonic waves to be treated by the different treatment. For example, such a method may be applied to a treatment in which a deep part is treated by being cauterized by converged ultrasonic waves while a shallow part, a tissue surface or the like is treated by being cauterized by laser light.

Figure 18:
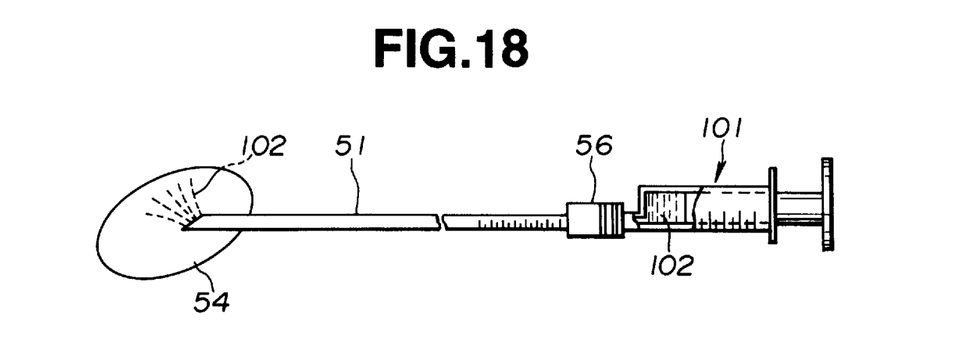
FIG. 18 is a diagram of the construction of an operating probe including a guide needle and a syringe, provided as operation means inserted into a treated part through an ultrasonic probe in accordance with a third embodiment of the present invention, showing an operation in a state where the operating probe is puncturing the treated part.

FIG. 18 illustrates another example of operation means inserted into a treated part through an ultrasonic probe in accordance with the third embodiment of the present invention.

In this embodiment, a medicament injection means is used as an operation means which is used in combination with an ultrasonic probe for making ultrasonic diagnosis and treatment and which is inserted into a body cavity through the ultrasonic probe to reach a treated part to perform an operation. FIG. 18 is an illustration for an operation showing the construction of a probe for a treating operation provided as an operation means and including a guide needle and a syringe, and showing a state where the probe is puncturing a treated part.

A guide needle 51 which is inserted into a body cavity through the ultrasonic probe having a guide for operation means, as in the first embodiment, is arranged so that a syringe 101 can be attached to a connector portion 56 on the operator side. The guide needle 51 is used as a needle for injecting a medicament. The syringe 101 contains a medicament liquid 102. The medicament liquid 102 can be injected into a lesion part 54 through the guide needle 51 by the syringe 101.

For example, a medicament such as a carcinostatic substance, an ultrasonic enhancer (e.g., emulsion or the like) or an ultrasonic enhancer combined with a tumor collecting material (e.g., fluorodeoxyglucose) is used as medicament liquid 102.

In this embodiment, the guide needle 51 is led through the ultrasonic probe to reach and puncture the lesion part 54 while optical observation and ultrasonic observation of the target part in the body cavity are made, as in the first embodiment. Puncturing is confirmed through the observation image on the monitor, and medicament liquid 102, i.e., a medicament such as a carcinostatic substance, an ultrasonic enhancer or an ultrasonic enhancer combined with a tumor collecting material, is injected into the lesion part 54 from the syringe 101 connected to the guide needle 51. Thereafter, strong ultrasonic waves are converged at the lesion part 54 by the treating ultrasonic vibrator in the ultrasonic probe, thus performing a treating operation with ultrasonic waves.

In this embodiment, as described above, a medicament such as a carcinostatic substance, an ultrasonic enhancer and the like can be injected into the treated part in the diseased part, and it is possible to dose the lesion part with a carcinostatic substance or the like as well as to strengthen treating ultrasonic waves at the treated part. Consequently, the treatment of this embodiment has an improved effect of treating the diseased part in comparison with the treatment only with ultrasonic waves from the ultrasonic vibrator.

It is also possible to make a biopsy under the guidance of ultrasonic diagnosis with an ultrasonic probe by setting a suction biopsic needle in place of the guide needle. An example of an arrangement in which a tissue picking means including biopsic forceps such as a suction biopsic needle is used as an operation means will be described as the fourth embodiment of the present invention.

Figure 19:
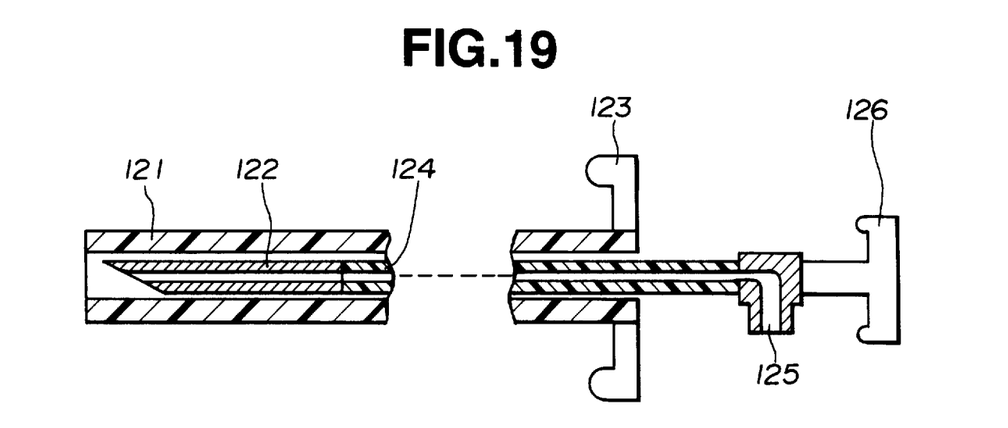
FIG. 19 is a cross-sectional view of the construction of an operating probe including a suction biopsic puncturing needle, provided as operation means inserted into a treated part through an ultrasonic probe in accordance with a fourth embodiment of the present invention.

FIG. 19 is a cross-sectional view of the construction of an operating probe including a puncturing needle for suction biopsy as an operation means inserted into a treated part through an ultrasonic probe in accordance with the fourth embodiment of the present invention.

The suction biopsic needle is constructed by accommodating a hard hollow puncturing needle 122 in a soft outer tube 121. A grip A 123 is connected and fixed to a rear end portion of the soft outer tube 121. A soft tube 124 is connected to a rear end portion of the puncturing needle 122. A suction port (opening) 125 and a grip B 126 are connected to a rear end portion of the tube 124. A continuous communication path extends through the suction port and a lumen of the tube 124 to the extreme end of the puncturing needle 122. The suction port 125 has a size and a structure such as to be able to be connected to an extreme end of a syringe (not shown). In a state prior to use, the grip A 123 and the suction port 125 are spaced apart from one another by a distance of about 50 mm.

A puncturing biopsy is conducted under ultrasonic guidance with the suction biopsic needle thus-arranged and in accordance with a procedure described below.

First, an examined part is depicted as an ultrasonic image, and the suction biopsic needle is inserted through the insertion opening of the ultrasonic probe. The suction biopsic needle is passed through the channel inside the ultrasonic probe and projects out of the channel opening provided in the extreme end section of the probe. As the suction biopsic needle is inserted into the channel, the extreme end of the suction biopsic needle is brought into contact with the lesion part surface by the guide for operation means, as in the above-described embodiments.

In this state, the grip B 126 is pushed in by gripping the grip A 123 to cause the puncturing needle 122 to project out of the extreme end of the outer tube 121 to puncture the lesion part. The state of the puncturing needle 122 reaching the target part is confirmed through the ultrasonic image.

Next, the syringe (not shown) is connected to the suction port 125 and the plunger in the syringe is drawn outward to suck the interior of the puncturing needle 122. At this time, materials in the lesion tissue are collected in the syringe through the puncturing needle 122, the tube 124 and the suction port 125.

Thus, in this embodiment, a biopsy of the lesion part can be made by using the suction biopsic needle while a treatment with ultrasonic waves is being conducted, thereby enabling the states of the tissue prior to and after treatment to be examined.

Figure 20:
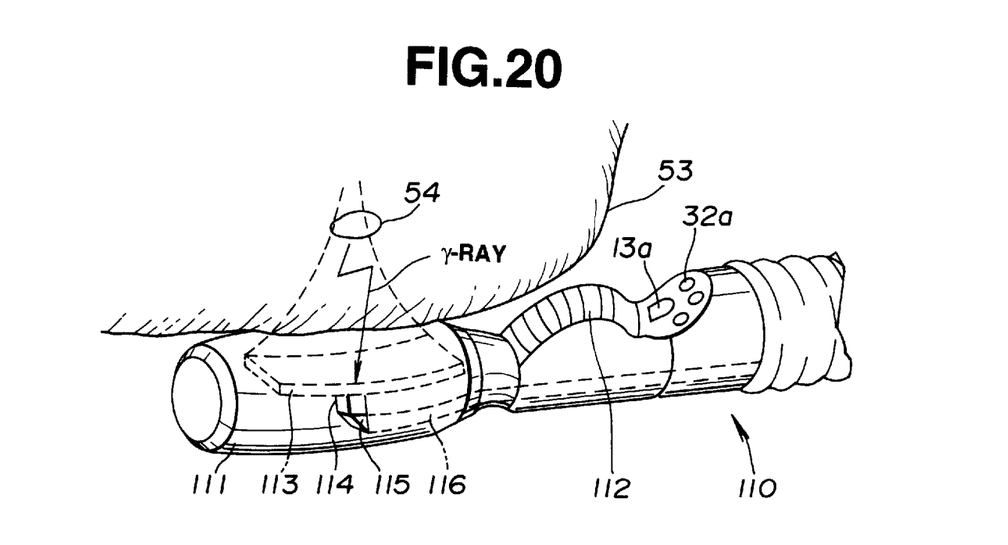
FIG. 20 is a diagram of an example of the construction of an extreme end portion of an ultrasonic probe having a γ ray detection means for detecting γ rays from a lesion part.

FIG. 20 illustrates an example of an arrangement using an ultrasonic probe to which the construction of an endoscope is applied and which is provided with a γ-ray detection means for detecting γ rays from a lesion part.

The ultrasonic probe of this embodiment is arranged by being adapted to the construction of the inserted portion of the endoscope, as in the case of the first embodiment. An ultrasonic vibrator is provided in an extreme end section of the probe. As illustrated in FIG. 20, a forward obliquely viewing type optical observation means (not shown) is provided inside an observation window 32a in an extreme end section 111 of the ultrasonic probe 110, a channel opening 13a for projecting an operating instrument or the like is provided in the vicinity of the observation window 32a, and a convex type observing ultrasonic vibrator 112 is provided on the extreme end side of the observation window 32a and the channel opening 13a. Also, a treating ultrasonic vibrator 113 is provided in the probe extreme end section 111 on the extreme end side of the observing ultrasonic vibrator 112.

Further, in the probe extreme end section 111, a scintillator 114 which emits light by detecting γ rays in a certain direction and a prism 115 disposed in abutment against the scintillator 114 are provided on the reverse side of the treating ultrasonic vibrator 113. Optical fibers 116 for guiding light from the scintillator 114 to the probe operator side are provided in the inserted portion. The optical fibers 116 extend to an operating portion (not shown) on the operator side, and a photoelectric converter unit (not shown) is disposed so as to face a base end portion of the bundle of optical fibers 116 to convert light from the scintillator 114 into an electrical signal.

To make diagnosis and treatment by using the ultrasonic probe 110 of this embodiment, a patient is first injected slowly with a medicament in which a material radiating γ rays, such as gallium (Ga) or fluorine (F), is combined with a tumor collecting material such as fluorodeoxyglucose. This medicament is accumulated in a tumor part (lesion part 54) such as cancer in organic tissue 53 to release γ rays. Next, the ultrasonic probe 110 is inserted into the body cavity, and the lesion part 54 and other regions in the vicinity of the lesion part 54 are observed optically and through ultrasonic waves by using the optical observation means and observing ultrasonic vibrator 112.

At this time, since γ-rays are radiated from the lesion part 54, the scintillator 114 detects γ rays and emits light when the extreme end section 111 of the ultrasonic probe 110 is brought closer to the lesion part 54. The light from the scintillator 114 is received by the photoelectric conversion unit (not shown) through the optical fibers 116 to be converted into an electrical signal indicating that the probe extreme end section 11 has been brought close to the lesion part 54. By this output signal from the photoelectric conversion unit, the operator is informed of the state of the probe extreme end section 111 being brought close to the lesion part 54.

Since the scintillator 114 has a directionality in detecting γ rays, the extreme end section 111 of the ultrasonic probe 110 is made to face in the direction toward the lesion part 54 on the basis of information on the intensity of γ rays detected by the scintillator 114. The direction in which treating ultrasonic waves are emitted from the treating ultrasonic vibrator 113 is thereby set so as to coincide with the lesion part 54. Then the lesion part 54 is irradiated with strong ultrasonic waves from the treating ultrasonic vibrator 113, thus performing a treating operation with ultrasonic waves.

As described above, a means for detecting γ rays from a lesion part such as cancer is provided to enable the extreme end section of the ultrasonic probe having an ultrasonic vibrator to face accurately in the direction toward to a lesion part such as cancer, thereby improving the directionality to the treatment object part. It is therefore possible to improve the treatment efficiency.

It is apparent that, in the present invention, various modifications of the above-described embodiments may be made without departing from the spirit and scope of the invention, and it will be understood that the invention is not limited to the disclosed embodiments except as defined in the appended claims.

What is claimed is:

1. An ultrasonic diagnosis and treatment system for performing observing and treating operations using ultrasonic waves, said system comprising:

a thin tube insertable into a body cavity;

an ultrasonic observing means emitting sequential scanning ultrasonic waves for observing internal body regions so as to detect treated parts therein;

an ultrasonic treating means for emitting strong ultrasonic waves for treatment to be converged on said treated parts, said ultrasonic treating means and said ultrasonic observing means being provided at an extreme end of said thin tube, said ultrasonic treating means including plurality of ultrasonic radiating devices oriented to converge said ultrasonic waves for treatment in a region observed by said ultrasonic observing means;

operation means for simultaneously performing an operation other than the treating operation using the ultrasonic waves on at least said region observed by using the ultrasonic waves; and a guide provided on said thin tube to enable said operation means to reach said region observed by using the ultrasonic waves.

2. An ultrasonic diagnosis and treatment system according to claim 1, wherein said operation means is adapted to perform an operation other than the treating operation using the ultrasonic waves by at least puncturing the region observed by using the ultrasonic waves.

3. An ultrasonic diagnosis and treatment system according to claim 1, wherein said operation means comprises treating operation means for performing a treating operation other than the treating operation using the ultrasonic waves in association with the treating operation using the ultrasonic waves at least in a treatment target part including the region observed by using the ultrasonic waves.

4. An ultrasonic diagnosis and treatment system according to claim 3, wherein said treating operation means is adapted to perform an auxiliary treating operation in association with the treating operation using the ultrasonic waves.

5. An ultrasonic diagnosis and treatment system according to claim 3, wherein said treating operation means comprises a guide needle having a hollow guide tube, and a treating probe passed through said guide needle and projected from an extreme end of said guide needle to perform said treating operation.

6. An ultrasonic diagnosis and treatment system according to claim 3, wherein said treating operation means comprises a microwave radiating probe for emitting microwaves to said treatment target part to perform a treating operation.

7. An ultrasonic diagnosis and treatment system according to claim 3, wherein said treating operation means comprises a laser probe for emitting laser light to said treatment target part to perform said treating operation.

8. An ultrasonic diagnosis and treatment system according to claim 3, wherein said treating operation means comprises cooling means for cooling said treatment target part to perform freezing treating operation.

9. An ultrasonic diagnosis and treatment system according to claim 3, wherein said treating operation means comprises heating means for heating said treatment target part to perform treating operation.

10. An ultrasonic diagnosis and treatment system according to claim 9, wherein said heating means comprises a high frequency current probe (HF probe) for making a treatment of cauterizing and solidifying an organic tissue by high frequency current.

11. An ultrasonic diagnosis and treatment system according to claim 9, wherein said heating means comprises a microwave probe (MW probe) for making a treatment of heating, cauterizing and solidifying an organic tissue by microwave electromagnetic waves.

12. An ultrasonic diagnosis and treatment system according to claim 9, wherein said heating means comprises a radio frequency electromagnetic wave probe (RF probe) for making a treatment of heating, cauterizing and solidifying an organic tissue by radio frequency electromagnetic waves.

13. An ultrasonic diagnosis and treatment system according to claim 9, wherein said heating means comprises a heating probe having heating means for making a treatment of heating and cauterizing an organic tissue.

14. An ultrasonic diagnosis and treatment system according to claim 1, wherein said operation means comprises assisting operation means for performing an operation other than the treating operation using the ultrasonic waves to assist the treating operation using the ultrasonic waves at least in a treatment target part including the region observed by using the ultrasonic waves.

15. An ultrasonic diagnosis and treatment system according to claim 14, wherein said assisting operation means comprises intracorporeal information detection means for detecting or monitoring various kinds of information on an internal body region in the vicinity of said treatment target part.

16. An ultrasonic diagnosis and treatment system according to claim 15, wherein said intracorporeal information detection means comprises a temperature detecting probe for detecting the temperature of said treatment target part.

17. An ultrasonic diagnosis and treatment system according to claim 15, wherein said intracorporeal information detection means comprises a sound pressure detecting probe for detecting the sound pressure at said treatment target part.

18. An ultrasonic diagnosis and treatment system according to claim 14, wherein said assisting operation means comprises tissue picking means for picking an organic tissue in the vicinity of said treatment target part.

19. An ultrasonic diagnosis and treatment system according to claim 14, wherein said assisting operation means comprises a medicament injecting means including a medicament injector needle for injecting a medicament into the body.

20. An ultrasonic diagnosis and treatment system according to claim 1, wherein said thin tube has a main portion formed of a flexible tubular member.

21. An ultrasonic diagnosis and treatment system according to claim 1, wherein said thin tube has a main portion formed of a hard tubular member.

22. An ultrasonic diagnosis and treatment system according to claim 1, wherein said thin tube has a curving portion capable of being curved.

23. An ultrasonic diagnosis and treatment system according to claim 1, wherein said thin tube is provided with optical observation means for performing observation by obtaining an optical image of an observed part.

24. An ultrasonic diagnosis and treatment system according to claim 1, wherein said guide includes a channel formed in said thin tube as an insertion passage through which operation means is passed, whereby an extreme end portion of said operation means is set at a predetermined angle such as to extend to the region observed by using the ultrasonic waves.

25. An ultrasonic diagnosis and treatment system according to claim 24, wherein said guide sets the extreme end portion of said operation means at a predetermined angle such that the extreme end portion of said operation means extends to a convergent point at which the treating ultrasonic waves emitted from said ultrasonic treating means are converged or to a point in the vicinity of said convergent point.

26. An ultrasonic diagnosis and treatment system according to claim 24, wherein a raising base for raising the extreme end portion of said operation means so that said extreme end portion of said operation means faces in the direction at the predetermined angle is formed in an extreme end portion of said channel.

27. An ultrasonic diagnosis and treatment system according to claim 24, wherein an insertion amount measuring means for measuring the amount of insertion of said operation means into said guide is provided on least one of said guide and said operation means guided by said guide to enable said operation means to be inserted by a predetermined amount.

28. An ultrasonic diagnosis and treatment system according to claim 1, wherein said guide is formed so as to include at least one of a guide groove and a guide hole which is provided in an extreme end portion of said thin tube and into which a portion of said operation means inserted into the body cavity separately of said thin tube is fittingly inserted, whereby the extreme end portion of said operation means is set at a predetermined angle such as to extend toward the region observed by using the ultrasonic waves.

29. An ultrasonic diagnosis and treatment system according to claim 1, wherein said guide comprises:
a directional member for setting the extreme end portion of said operation means at a predetermined angle such that the extreme end portion of said operation means extends toward the region observed by using the ultrasonic waves; and
projection amount measuring means provided on at least one of said guide and said operation means guided by said guide to measure the amount of projection of said operation means relative to the position to one of said ultrasonic observing means and said ultrasonic treating means on said thin tube.

30. An ultrasonic diagnosis and treatment system according to claim 1, wherein said thin tube is provided with a γ ray detection means having a directionality in the same direction as the direction in which the treating ultrasonic waves are radiated from said treating ultrasonic vibrator, and wherein the direction of a lesion part is detected by detecting, by said γ ray detection means, γ rays from a tumor collecting radioactive material dispensed in the body.

31. An ultrasonic diagnosis and treatment system for performing optical observation and performing observing and treating operations using ultrasonic waves, said system comprising:
a thin tube insertable into a body cavity;
an ultrasonic observing means emitting sequential scanning ultrasonic waves for observing internal body regions so as to detect treated parts therein;
an ultrasonic treating means for emitting strong ultrasonic waves for treatment to be converged on said treated parts, said ultrasonic treating means and said ultrasonic observing means being provided at an extreme end of said thin tube, said ultrasonic treating means including a plurality of ultrasonic radiating devices oriented to converge said ultrasonic waves for treatment in a region observed by said ultrasonic observing means;
optical observation means contained in said thin tube for obtaining an optical image of an observed region;
operation means for simultaneously performing an operation other than the treating operation using the ultrasonic waves on at least one of said region observed by using the ultrasonic waves and said region optically observed; and
a guide provided on said thin tube to enable said operation means to reach at least one of said region observed by using the ultrasonic waves and said region optically observed.

32. An ultrasonic diagnosis and treatment system for performing observing and treating operations using ultrasonic waves, said system comprising:
a thin tube insertable into a body cavity;
an ultrasonic observing means emitting sequential scanning ultrasonic waves for observing internal body regions so as to detect treated parts therein;
an ultrasonic treating means for emitting strong ultrasonic waves for treatment to be converged on said treated parts, said ultrasonic treating means and said ultrasonic observing means being provided at an extreme end of said thin tube, said ultrasonic treating means including a plurality of ultrasonic radiating devices oriented to converge said ultrasonic waves for treatment in a region observed by said ultrasonic observing means;

treating operation means for simultaneously performing another treating operation in association with the treating operation using the ultrasonic waves on at least said region observed by using the ultrasonic waves; and a guide provided on said thin tube to enable said operation means to reach said region observed by using the ultrasonic waves.

33. An ultrasonic diagnosis and treatment system for performing observing and treating operations using ultrasonic waves, said system comprising:

a thin tube insertable into a body cavity;

an ultrasonic observing means emitting sequential scanning ultrasonic waves for observing internal body regions so as to detect treated parts therein;

an ultrasonic treating means for emitting strong ultrasonic waves for treatment to be converged on said treated parts, said ultrasonic treating means and said ultrasonic observing means being provided at an extreme end of said thin tube, said ultrasonic treating means including plurality of ultrasonic radiating devices oriented to converge said ultrasonic waves for treatment in a region observed by said ultrasonic observing means;

assisting operation means for performing an operation other than the treating operation using microwaves to assist a treating operation using the ultrasonic waves at least on a region observed by using the ultrasonic waves; and a guide provided on said thin tube to enable said assisting operation means to reach said region observed by using the ultrasonic waves.

34. An ultrasonic diagnosis and treatment system for performing observing and treating operations using ultrasonic waves, said system comprising:

a thin tube insertable into a body cavity;

an ultrasonic observing means emitting sequential scanning ultrasonic waves for observing internal body regions so as to detect treated parts therein;

an ultrasonic treating means for emitting strong ultrasonic waves for treatment to be converged on said treated parts, said ultrasonic treating means and said ultrasonic observing means being provided at an extreme end of said thin tube, said ultrasonic treating means including a plurality of ultrasonic radiating devices oriented to converge said ultrasonic waves for treatment in a region observed by ultrasonic observing means;

laser treating operation means for simultaneously performing a laser treating operation in association with the treating operation using the ultrasonic waves on at least said region observed by using the ultrasonic waves; and a guide provided on said thin tube to enable said operation means to reach said region observed by using the ultrasonic waves.

* * * * *